(12) United States Patent
Nichols et al.

(10) Patent No.: US 6,453,946 B2
(45) Date of Patent: Sep. 24, 2002

(54) LONG LIFETIME FLUID SWITCHING VALVE

(75) Inventors: Jon A. Nichols, Santa Rosa; Burney L. Baron, Rohnert Park, both of CA (US)

(73) Assignee: Rheodyne, LP, Rohnert Park, CA (US)

( * ) Notice: Subject to any disclaimer, the term of this patent is extended or adjusted under 35 U.S.C. 154(b) by 45 days.

(21) Appl. No.: 09/800,320

(22) Filed: Mar. 6, 2001

Related U.S. Application Data (60) Provisional application No. 60/188,968, filed on Mar. 10, 2000.

(51) Int. Cl.$^7$ .............................................. F16K 11/074
(52) U.S. Cl. .................................. 137/625.15; 251/268
(58) Field of Search ..................... 251/368; 137/625.15, 137/625.11, 625.14, 625.46, 627

(56) References Cited

U.S. PATENT DOCUMENTS

| | | | | |
|---|---|---|---|---|
| 4,661,052 A | * | 4/1987 | Ruhle | .......................... 417/552 |
| 5,165,699 A | * | 11/1992 | Shrontz et al. | ................. 277/1 |
| 5,287,030 A | * | 2/1994 | Nutter | .......................... 310/89 |
| 5,296,145 A | * | 3/1994 | Allington et al. | ........... 210/541 |
| 6,012,488 A | * | 1/2000 | Nichols | ............. 137/625.15 X |
| 6,382,035 B1 | * | 5/2002 | Nichols | .................... 73/863.72 |

\* cited by examiner

*Primary Examiner*—Kevin Lee
(74) *Attorney, Agent, or Firm*—Leon D. Rosen (57) ABSTRACT

A rotary fluid switching valve has facewise adjacent rotor and stator faces of materials that result in an exceptionally long lifetime. One face is of a fluorocarbon-containing polymer, while the other face is Tungsten Carbide/Carbon (WC/C). The WC/C coating is preferably on a metal stator which has machined ports to accept tubing fittings that connect to stator passages that extend to the interface of stator and rotor.

7 Claims, 6 Drawing Sheets

FIG. 1  FIG. 2

FIG. 3A
(PRIOR ART)
316 SS
ON VESPEL

FIG. 3B
WC/C
ON VESPEL

LONG LIFETIME FLUID SWITCHING VALVE

CROSS-REFERENCE

Applicant claims priority from U.S. Provisional application 60/188,968 filed Mar. 10, 2000.

BACKGROUND OF THE INVENTION

Figure 1:
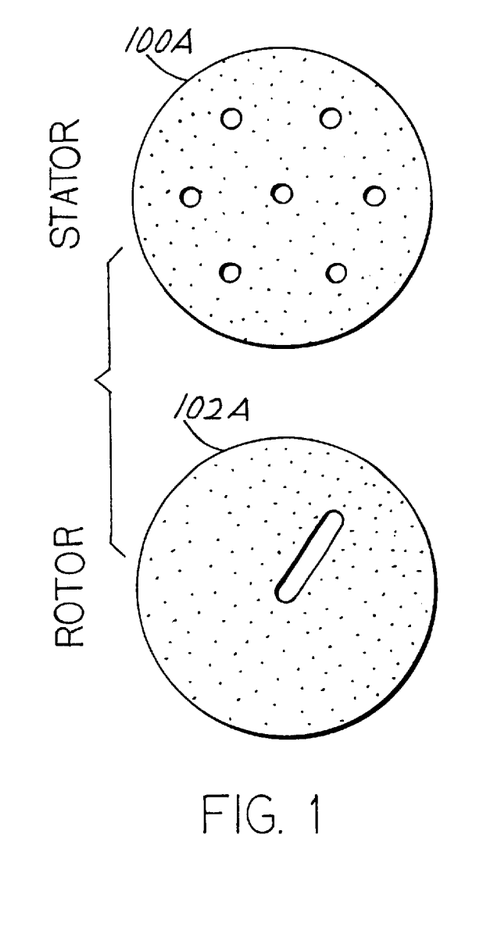
FIG. 1 is an exploded view of one configuration of a valve of the invention, showing the faces of the stator and rotor.
Figure 2:
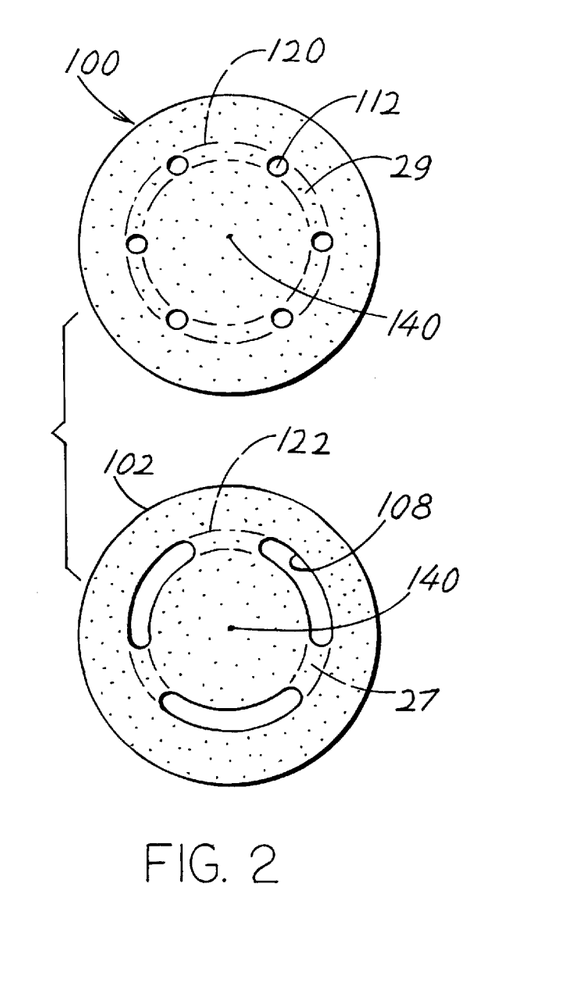
FIG. 2 is an exploded view of another configuration of a valve of the invention, showing the faces of the stator and rotor.

Many scientific instruments require fluid switching valves for functions such as solvent selection, fraction collection, fluid redirection, stream sampling, or sample injection. These valves must have small diameter passages, typically in the range of 0.005 to 0.1 inch, that are well aligned and without cavities ("dead volumes"), so as to minimize dispersion as samples and fluid elements pass through them. A common architecture is shown in FIG. 1, where the stator 100A has six peripheral passages and one central passage, and the rotor 102A has one radial passage, thereby allowing selection of one of six solvents for direction out the central port, depending on the rotational position of the rotor. Sometimes there are many more peripheral ports. Another common architecture is shown in FIG. 2, where the rotor 102 contains alternating peripheral grooves 108. There are many other switching patterns.

In addition to low dispersion, other desirable features for valves used as scientific instruments include high inertness, low friction, and long lifetime.

This last characteristic, long lifetime, which is typically measured in numbers of actuations, has become increasingly important during the last ten years. The cycle time of scientific analysis has shortened in order to become more productive. As a consequence, valves with a short lifetime require frequent maintenance to replace one or more of the sealing parts. Formerly such maintenance might be required every six months, but now it may be required every week when using conventional valves with high duty cycles. The down time caused by such maintenance is undesirable, as it becomes a significant expense and slows productivity.

Lifetime can be defined as the number of actuations, or in the case of two-position valves, the number of cycles between position A-to-B-to-A, before the sealing parts need to be replaced due to excessive leakage. The amount of leakage that can be tolerated varies with the application. In one common use, high performance liquid chromatography using conventional columns at flow rates of 1 milliliter per minute, a leakage rate of 0.3 microliter per minute is commonly tolerated, but not one that is much larger, such as 3 microliters per minute.

Leakage can be from one or all of the ports or grooves radially outward to the extra-valve environment, i.e. to ambient, or leakage can be between ports which is called cross-port leakage. The latter is common and often is the more detrimental to function. For example, cross-port leakage in a valve used in the auto sampler of a liquid chromatograph can cause poor analytical precision due to errors in sample metering.

It should be understood that the type of valve under discussion does not have a two-state characteristic, leaking or not leaking. Rather, the amount of leakage is high when the fluid pressure is high, and is low when the fluid pressure is low, asymptotically approaching zero as the fluid pressure approaches zero. It is for this reason that the lifetime is described in terms of the leak rate exceeding a predetermined amount such as 0.3 microliter per minute at a predetermined fluid pressure such as 5000 psi.

The lifetime of the sealing is typically determined by adjusting the valve to hold a specified set pressure, while leaking no more than a specified rate, then cycling the valve and periodically testing its pressure holding capability. When this pressure holding capability drops a specified amount, the maximum lifetime is said to have been reached. For example, using a test apparatus, a valve is adjusted until it leaks 0.3 microliters per minute when pressurized to 5000 psi. It is then attached to an automated apparatus capable of repetitively actuating the valve. It is cycled 5,000 times, then returned to the test apparatus, where the pressure at which the leakage is no more than 0.3 microliters per minute is determined. The valve is again attached to the actuating apparatus and cycled another 5,000 times, after which it is again tested. This sequence is repeated until the pressure at which leakage is no more than 0.3 microliters per minute has dropped a specified amount. This specified amount might be, for example, 500 psi, which is 10% of the original set pressure. If the pressure required to keep the leak rate below 0.3 microliters per minute dropped to 4,500 psi after 20,000 cycles, and below 4,500 psi after 25,000 cycles, this valve would be said to have a lifetime of 20,000 cycles.

It is common to use a stator of metal such as stainless steel, so tubing connections can be attached in threaded holes, and to use a rotor of fluorocarbon-containing plastic for low friction sliding against the metal under a clamping force that presses the surfaces together at slightly more than the pressure of the fluid. Cross-port leakage is thought to be caused by scratches or depressions in the surface of the stator and/or rotor that form leak grooves. Such leak grooves provide a path for fluid flow when there is a pressure gradient between the ports. Lifetime is increased by delaying the onset, reducing the number, and minimizing the size of such leak grooves. In valves that are the subject of this invention, the design of surfaces to maximize lifetime is difficult to do from first principles. This is because, as is commonly understood, the subject of wear of plastic parts is of considerable complexity. An understanding of wear, and its related tribological (study of friction and wear) topics of friction and lubrication, involves topics such as asperity deformation, adhesion, modes of energy dissipation, molecular relaxation times, etc., each in itself a complex subject.

The limitations of the science of tribophysics cause the invention of longlife valves of the type being discussed to be driven by experimentation using a large variety of materials and surface treatments that would not necessarily be expected to produce good results. Indeed, in the experience of the inventors, little is predictable in the art of making valves.

For example, ceramic is an extremely wear resistant material that has been used as a counterface against polymeric rotors. However, the polymers that exhibit long lifetime against ceramic must be determined experimentally. Furthermore, when certain polymers are used as rotors and run against polished ceramic, the presence in the ceramic of relatively large pits does not necessarily cause excessive wear and short lifetime. Conversely, some extremely smooth ceramic surfaces cause high wear.

There are ceramic-polymer seal combinations that have long lifetimes. However, making a stator of ceramic is costly, primarily due to the size and complex shape, including the threaded ports. As an alternative, a ceramic stator face assembly can be placed on a metal stator, to provide long lifetime, as in the model 7750E-020 valve made by Rheodyne, L. P. The stator face is a ceramic plate that is sealed by a static seal to the face of a metal body, with the ceramic plate and metal body having aligned passages. The cost of such a stator face is less than the cost of a totally ceramic stator. However, this additional part adds volume to the valve passages, which increases dispersion. In some applications the added dispersion cannot be tolerated. It also results in an additional (static) sealing interface between the stator face and the bulk stator (metal body), which sometime requires that additional axial force be used on the stack of parts, in order to assure a fluid-tight static seal.

If the rotor is made of ceramic the cost is less than a ceramic stator, but the stator must then be the polymer part, which is problematic because it is too weak a material to use with common tubing fittings. As an alternative, a polymer stator face assembly can be placed onto a metal stator. However, this again adds volume and an additional sealing interface.

As a different type of example of the difficulty of making scientific instrument valves that have a long life, consider the design of the recently introduced EXL Technology valves made by Valco Instruments Co., Inc. This valve tries to achieve long lifetime by using some of the best materials, but which are still inadequate in life time when run at high pressure. Instead of trying to solve the lifetime problem with improved materials, the EXL Technology uses passive feedback, whereby the fluid pressure itself is used to help achieve the sealing force between the rotor and stator. The sealing force is limited to the active system pressure. For example, when the valve is operating at 5000 psi, a high force is used; when operating at only 2000 psi a lower force is used. However, the design of this valve necessitates that the fluid is connected by a tee to some non-switching stream volumes within the valve. These regions of the valve should not usually be exposed to the flowing stream, because of a concern for contamination and/or dead volume.

A rotary fluid valve which had a very long lifetime, which could be constructed at moderate cost, and which did not unduly increase the passage lengths, would be of value.

SUMMARY OF THE INVENTION

In accordance with one embodiment of the present invention, a rotary fluid switching valve is provided that has an exceptionally long life. The valve has a stator and rotor with sealing faces that press against each other with a high force as the stator pivots. One of the sealing faces is made of Tungsten Carbide/Carbon, referred to herein as WC/C, and the other is made of a fluorocarbon polymer. These two materials pressing against each other with a high pressure, as one slides on the other, were found to have an exceptionally long lifetime.

The WC/C is preferably a coating containing tungsten carbide particles in a soft amorphous carbon matrix. WC/C is preferably a plating on a metal stator body, such as stainless steel, with the body having machined threaded ports for connection to tube fittings. The stator is preferably formed of the fluorocarbon polymer. The polymer can be a solid fluorocarbon polymer, or a non-fluorocarbon polymer containing a fluorocarbon filler.

The novel features of the invention are set forth with particularity in the appended claims. The invention will be best understood from the following description when read in conjunction with the accompanying drawings.

DESCRIPTION OF THE PREFERRED EMBODIMENTS

In accordance with the invention, applicant has discovered that long valve lifetime results from the use of a rotor surface and stator surface, one of which is a fluorocarbon-containing polymer and the other a Tungsten Carbide/Carbon (WC/C) composition. In all cases, the surfaces were polished to a surface finish on the order of magnitude of one microinch, and actually about one microinch.

Figures 6, 7:
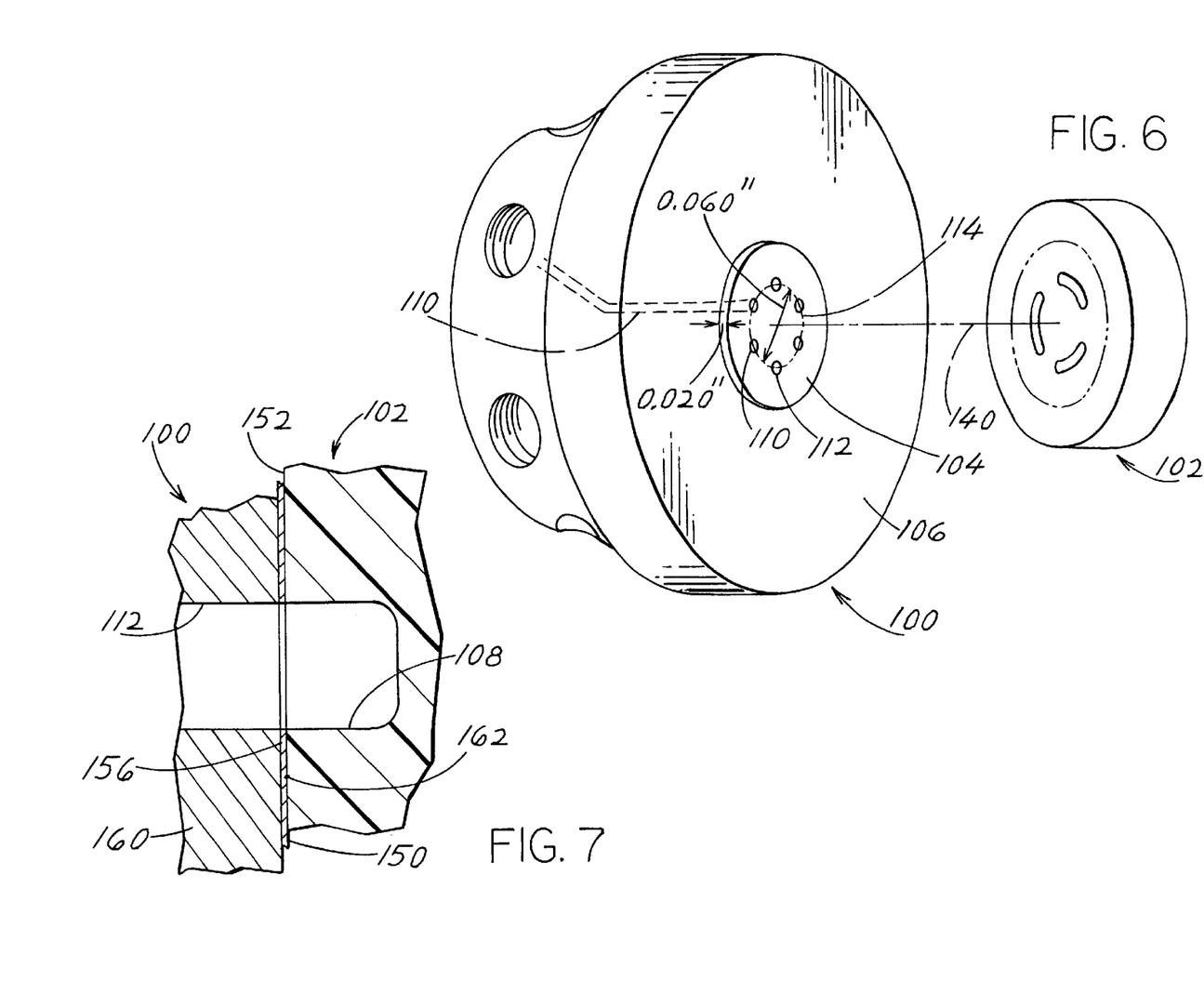
FIG. 6 is a simplified exploded isometric view of the valve of FIG. 2.
FIG. 7 is a partial sectional view of the valve of FIG. 6, with the stator and rotor faces pressing against one another.

FIG. 6 is an exploded isometric view of a stator 100 and rotors 102 that applicant has constructed and tested, with the stator being only of stainless steel or stainless steel with a WC/C coating, and with the rotor being of Vespel SP-211. The stator has a boss 104 that is raised from the surrounding surface 106. In valves that applicant constructed and tested, the stator had six passages 110 with proximal ends 112 lying on a circle 114 of 0.060 inch diameter or 0.080 inch diameter. FIG. 1 shows one possible pattern for the stator 100A and rotor 102A, while FIG. 2 shows the pattern for the particular stator 100 and rotor 102 of FIG. 6. The stator passage proximal ends 112 each have a diameter of 0.008 inch, and lay on a band-shaped area 29 of 0.008 inch width. The rotor grooves 108 each lie on a band-shaped area 27 of the land 122, which has a band width of 0.008 inch. The passage proximal ends and the grooves, lie on a radius from the axis of rotation 140.

In this discussion, we use the term fluorocarbon-containing polymer to include (i) polymers that are themselves a fluorocarbon (the continuous matrix phase), an example being Tefzel (ethylene tetrafluoroethylene), and (ii) polymers that are not fluorocarbons (the continuous matrix phase), in which one or more fillers (the discontinuous phases) have been added, one of which is a fluorocarbon polymer. An example of this second type is the DuPont polymer Vespel SP-211 (a polyimide containing 10% Teflon and 15% graphite filler). A fluorocarbon polymer is a polymer (long chain molecules) that include flourine and carbon.

We found that when a Vespel SP-211 rotor was run directly against a well polished 316 stainless steel stator (hereafter called SS), the pressure holding capability typically dropped from 6000 psi (the initial set pressure) to less that 4000 psi in 10,000 cycles. When the same polymer rotor material was run against an identical SS stator, which had been coated with WC/C (and subsequently polished), the pressure holding capability after 100,000 cycles varied between 5,500 and 6,500 psi. Note that some WC/C valves actually improved in performance with use. One valve was run for 200,000 cycles and the pressure holding capability dropped below 4000 psi; thus, the lifetime appears to be high but limited even for the WC/C valves.

The particular tungsten carbide coating that gave this performance was a Tungsten Carbide/Carbon coating with the trade name Balinit C, a product of the Balzers company. It is comprised of hard tungsten carbide particles in a soft amorphous carbon matrix. It is a composite coating that has a 1 to 5 micron thick lamellar structure of alternating layers of amorphous carbon and Tungsten Carbide particles.

This outstanding performance has never before been observed in our research laboratory when a polymeric rotor was run directly against a steel or a steel coated with a hard layer such as Titanium Nitride, except when the stator was covered with a bulk ceramic stator face. However, as discussed above, a bulk ceramic stator face has several disadvantages, including the high cost of a solid stator and the problem of static sealing of a stator cover to a metal body. To try to understand the reason for a long lifetime with a WC/C coating, we examined the rotor and stator surfaces before and after cycling, using an optical microscope and a profilometer. The results of this examination show that there are different wear patterns of the SS and of the WC/C surface, which we would not have predicted, as described below.

FIG. 7 shows the faces 150 and 152 of the stator 100 and rotor 102 respectively that press against one another with a high pressure (the maximum design pressure is on the order of magnitude of 2000 psi with 5000 psi being the most common). The WC/C coating 156 lies on a stainless steel body 160. The faces engage one another at an interface 162.

In this discussion, the region of the rotor or stator which is likely to give rise to cross-port leakage is called the "land." In the case of the stator, the land indicated at 120 in FIG. 2, is the ring-shaped surface area between the port holes that is an arc at the same average radius as the hole pattern of the stator. In the case of the rotor, the land, indicated at 122, is the surface between the grooves that is an arc at the same average radius as the grooves. The radially inner and outer edges of the stator hole pattern and rotor grooves are at the same radius.

In this discussion the removal of polymeric material from the rotor and its deposition onto the surface of the stator is called plating. Such plating is an indication of wear. It can cause the now roughened surface of the stator to in turn wear the rotor.

Figure 3A:
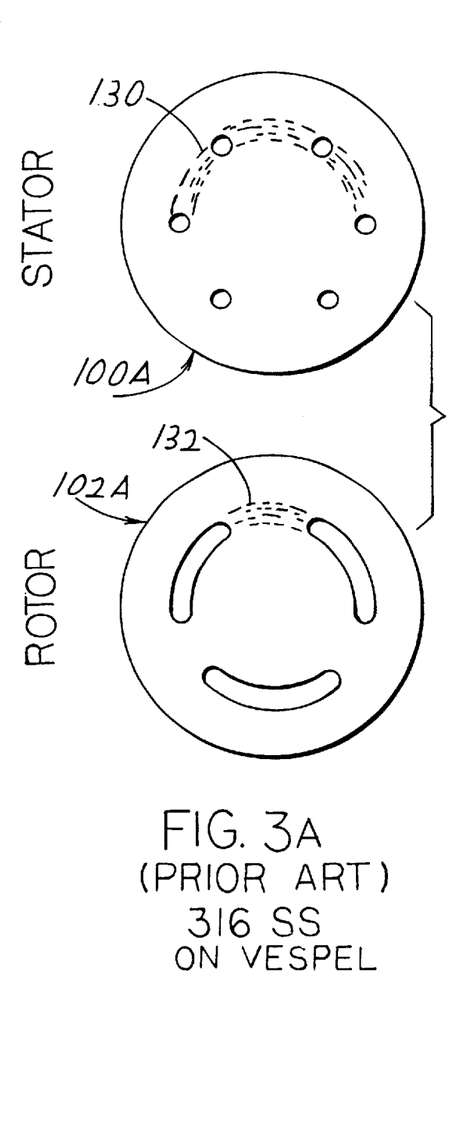
FIG. 3A is an exploded view of a prior art valve with a 316 stainless steel stator that pressed against a Vespel rotor, showing scratches on the surfaces after 10,000 cycles, in about the ten o'clock to two o'clock region.

Microscopic examination of the Vespel rotor run against a SS stator, after only 10,000 cycles, showed scratches in the land, in the form of arcs between the grooves. Likewise, the stator showed scratches in the land. This is illustrated in FIG. 3A where 130 shows scratches in the stator and 132 shows scratches in the rotor (only scratches along a limited angle are shown). Similar examination of the Vespel rotor run against the WC/C stator showed the lands 126, 124 to be clean and smooth after 10,000 cycles.

Figure 3B:
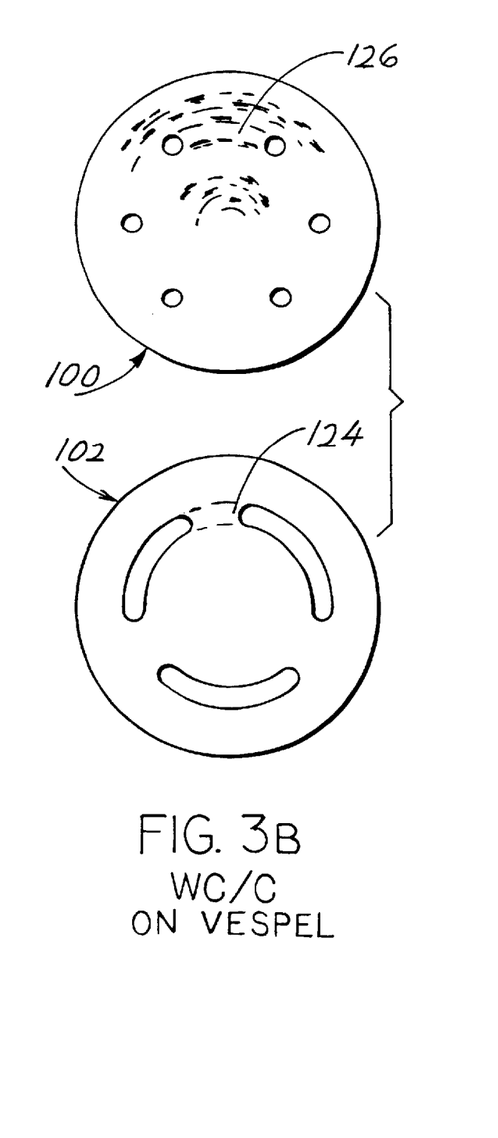
FIG. 3B is an exploded view of a valve of the present invention with WC/C at the stator face and Vespel fluorocarbon polymer at the rotor face, showing the locations of scratches and platings after 100,000 cycles of operation, in about the ten o'clock to two o'clock region, with scratches shown by thin lines and plating by thicker lines.

Further contrast in performance of the two materials is most notable when the WC/C material was examined after 100,000 cycles (the SS stator could not be tested beyond 10,000 cycles due to excessive leakage). This is illustrated in FIG. 3B. The land of the rotor had no wear, and there was only slight wear at radiuses less than and greater than the hole pattern radius. The land of the stator still had neither scratches nor plating. Yet at radiuses less than or greater than the hole pattern there was some scratching and considerable plating. The land of the WC/C stator was remarkably smooth, although it was slightly depressed. We have no explanation for this pattern of abrasion and plating. The lack of scratches extending to the passages and grooves, results in no large increase in leakage.

Examination of the surfaces was also done with a profiliometer (model TSK Surfcom S1400D). This instrument can measure surface roughness as well as vertical displacement. It can thus show the surface profile.

Figure 4A:
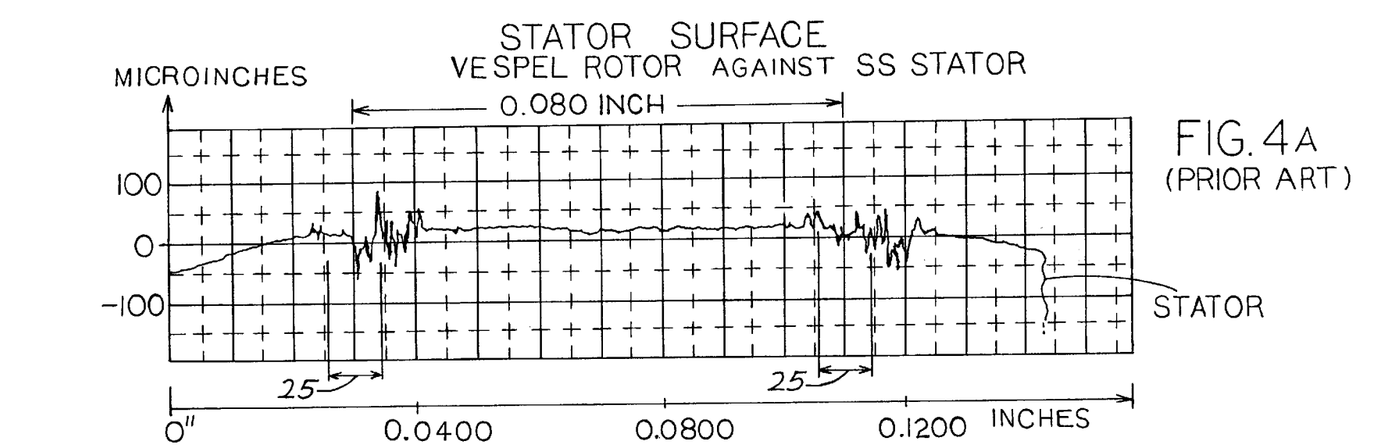
FIG. 4A is a graph showing variation in surface height with horizontal distance for a surface profile scan taken of the prior art stainless steel stator of FIG. 3A after 10,000 cycles, with the scan starting at one side of rotor and scanning across its diameter.
Figure 4B:
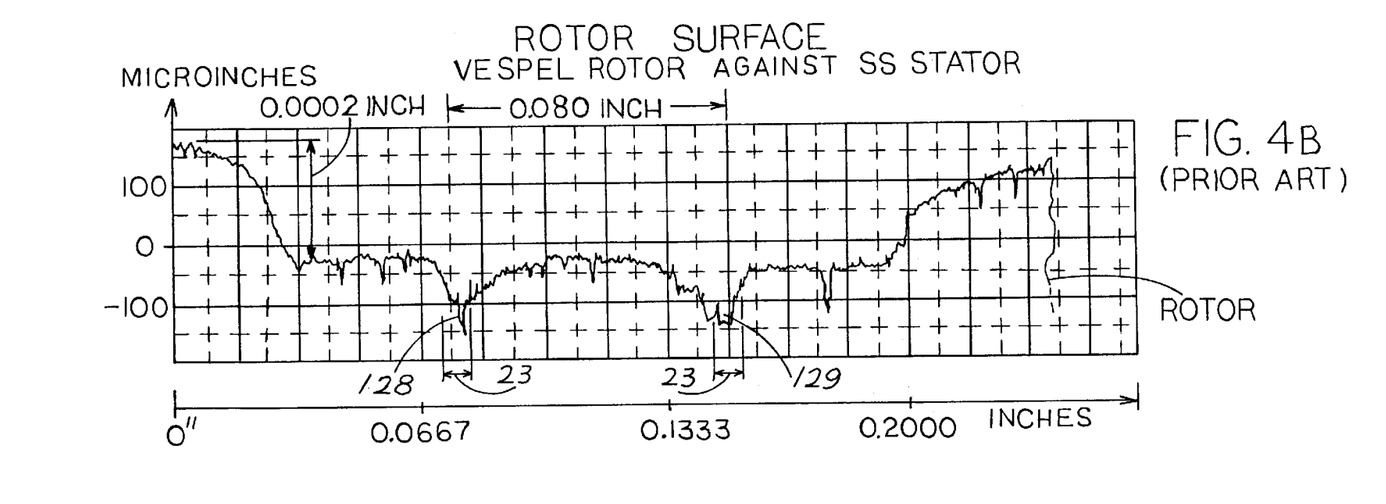
FIG. 4B is a graph showing variation in surface height with horizontal distance for a scan taken across the diameter of the prior art Vespel rotor of FIG. 3A after 10,000 cycles.

FIG. 4B shows the profile of a scan for a typical Vespel rotor that has run against a SS stator at 10,000 cycles. The stator passage ends lie on a circular band area 23 of 0.008 inch band width, with the band having an average diameter of 0.080 inch. We scanned across a diameter of the rotor. Starting at the left, the profile of the Vespel rotor starts at an unworn surface on the edge, drops down into the depression made by the 0.178 inch diameter boss of the mating stator, drops down further into the wear grooves 23 on the stator's 0.080 inch diameter hole pattern, and then rises up out of the depression to a relatively unworn surface in the center of the rotor. The depression is about 0.0002 inch deep and the wear troughs such as 128, 129 are almost 0.0001 inch deep. The overall shape of the depression matches the shape of the stator boss. The scan avoids the grooves in the rotor, i.e., it runs across the land or sealing surface between the pressurized grooves. Any channels or troughs in this region will be a leak path which will lower the holding pressure of the valve.

FIG. 4A shows the profile of the SS stator at 10,000 cycles, showing troughs at the lands 25 which are each of 0.008 inch width. Calculations from the theory of pressure drop in tubes of circular cross section under laminar (Poiseuille) flow show that a round trough of 0.000055 inch diameter and 0.030 inch length will pass water at room temperature at a flow of about 0.3 microliter per minute when the pressure difference from end to end is 5,858 psi. The measured troughs of FIGS. 4A and 4B are of the same magnitude and are thus likely to cause failure.

Figure 5A:
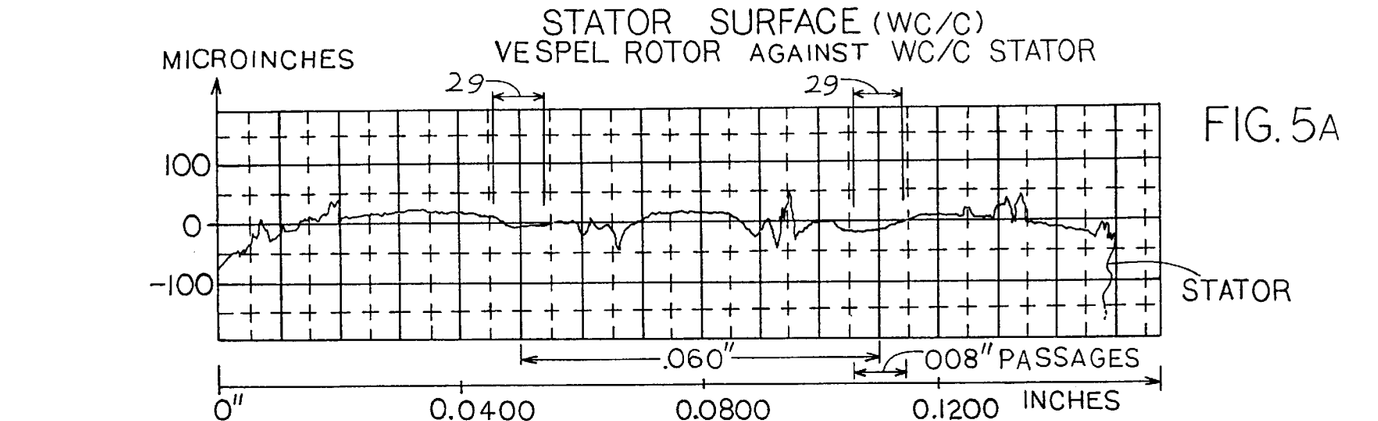
FIG. 5A is a graph showing variation in surface height with horizontal distance for a scan taken across the diameter of the WC/C stator of FIG. 3B.
Figure 5B:
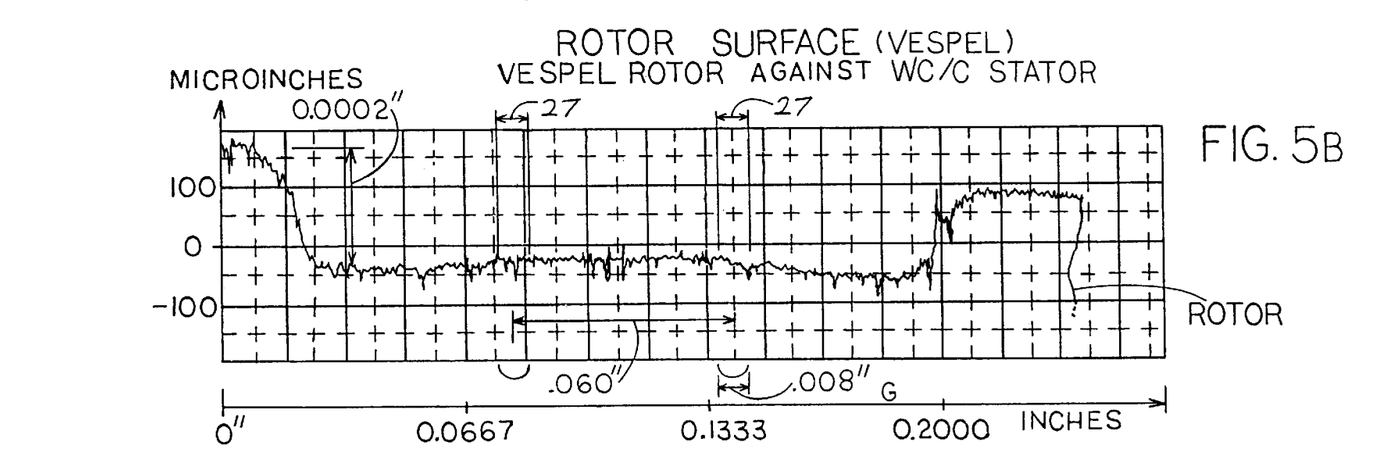
FIG. 5B is a graph showing variation in surface height with horizontal distance for a surface profile scan taken across the diameter of the Vespel rotor of FIG. 3A after 100,000 cycles, when used with the WC/C stator of FIG. 3B.

FIG. 5A shows the profile for a substantially identical rotor, but run against a WC/C coating on the stator, and in this case after 100,000 cycles. In this case, the stator passage ends lie on a circle of 0.060 inch diameter. The circular band areas 27 of 0.008 inch are indicated. The stator surface is shown in FIG. 5B with the band areas indicated at 29. Most noteworthy is the unusual surface characteristics of the stator. There is adhered polymer in most areas except between the holes. This plating damaged the rotor except in the critical areas between the grooves.

Typically the WC/C surface is on the stator, and the stator bulk material is stainless steel. Alternatively, the WC/C surface can be on the rotor, and the stator can be polymeric.

The valves can be a single-interface type, as illustrated previously, or a multiple-interface (sandwich valve) type, wherein there are multiple stators and rotors. In the simplest embodiment, a single rotor is sandwiched between two stators, as in Rheodyne model 7520.

Figure 8:
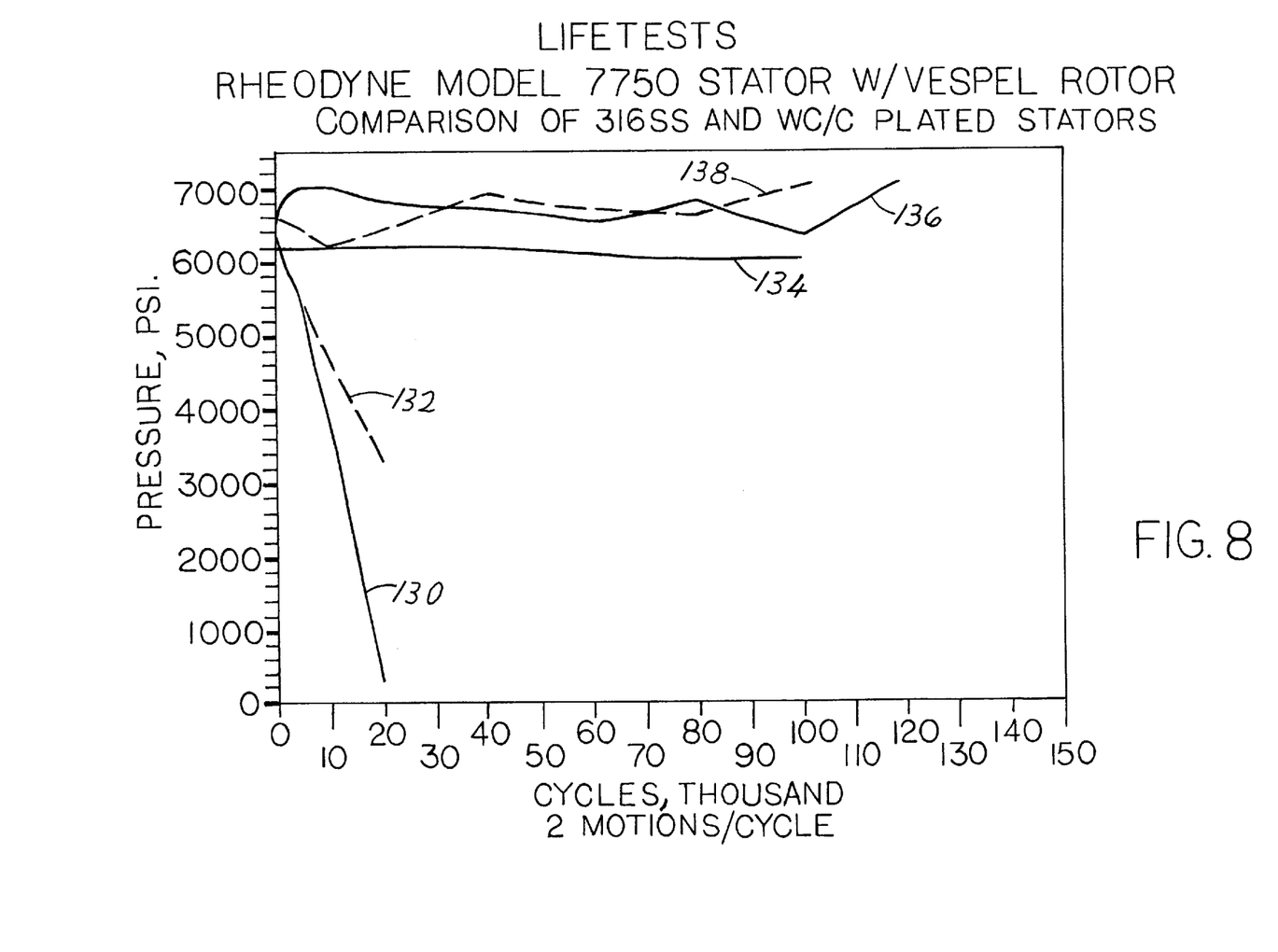
FIG. 8 is a graph showing variation in pressure for a leak rate of 0.3 microliters per minute, with the number of cycles of operation, for two prior art valves, and for three valves of the present invention.

FIG. 8 shows variation in maximum pressure level that can be maintained, with a leak rate of no more than 0.3 microliters per minute for stator passage ends lying on a circle of 0.100 inch diameter and spaced 60° apart, for a Vespel SP-211 rotor against a stainless steel stator surface, and against a WC/C stator surface. Results for two valves with stainless steel stator faces are indicated at 130 and 132. Results for three valves with WC/C coatings on their stator faces are indicated at 134, 136 and 138. It can be seen that for the stainless steel stator, the maximum pressure dropped below 5000 psi at about 10,000 cycles. However, for the stators with WC/C coatings at their interface, the maximum pressure remained above 6000 psi for up to 100,000 cycles.

Applicants have previously conducted tests of different stator face coatings against Vespel. Vespel SP-211, which is a polymide with 10% Teflon and 15% Graphite as fillers, has been used by applicant for the rotor. This is because the Vespel has the chemical resistance and low friction characteristics of Teflon (fluorocarbon based polymer) but avoids the tendency of Teflon to shed. Other fluorocarbons that do not shed can be used. In the tests, applicants used rotors with coatings of titanium nitride, chromium oxide, and other hard materials against the Vespel, but found that the lifetime was only slightly greater than for stainless steel. Only when applicant used the Tungsten Carbide/Carbon coating, did the lifetime increase by at least an order of magnitude. It is noted that the Balinit C Tungsten Carbide/Carbon coating has been used to coat metal cutting tools such as twist drills, and to coat components that slide against steel parts such as gears, pistons, and rollers in industrial machines. Applicant does not know of any use of a Tungsten Carbide/Carbon coating against a fluorocarbon polymer.

It may be noted that the force with which the stator is pressed against the rotor at the interface, can be varied so the pressure of the stator against the rotor is slightly more (e.g. 50 psi more) than the pressure at which fluid passes through the valve.

It is noted that for fluid switching valves of the present invention, the passages in the stator each have a diameter of less than 0.25 inch, and usually no more than 0.1 inch, to minimize the amount of fluid that is carried. Also, the valves are able to operate at pressures of over 100 psi.

Thus, the invention provides fluid switching valves, wherein the stator is formed of material that is easily machined to have threaded ports, etc., and where the pressure-contacting surfaces of the stator and rotor are constructed for a very long lifetime of operation. That is, the leak rate is maintained within acceptable limits (e.g. no more than 0.3 microliter per minute of 5000 psi) through many rotor switchings (e.g. much more than 10,000 cycles). One of the slideably engaging surfaces such as that of the rotor, is a fluorocarbon-containing polymer, while the other, such as that of the stator, is a Tungsten Carbide/Carbon composition.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A fluid switching valve which includes a stator element with a stator element face that lies at an interface and which includes a rotor element with a rotor element face that lies at said interface against said stator element face, with said rotor element being mounted to rotate about an axis with respect to said stator element to rotate between each of a plurality of rotor element positions, wherein said stator element has a plurality of largely axially-extending passages with proximal ends lying at said stator element face and wherein said rotor element has at least one rotor channel with at least an end lying at said rotor element face, wherein:

a first of said element faces is formed of a polymer containing a fluorocarbon, and the second of said element faces is formed of a combination of tungsten carbide and carbon.

2. The valve described in claim 1 wherein:

said second element face is formed of tungsten carbide particles in an amorphous carbon matrix.

3. The valve described in claim 1 wherein:

said polymer is Vespel SP-211 sold by DuPont;

said second element face comprises tungsten carbide particles in an amorphous carbon matrix that comprises a Balinit C coating.

4. The valve described in claim 3 wherein:

said stator is said second element, and said second element includes a body of stainless steel, with said second element face having a surface polish of at least on the order of five microinches.

5. The valve describe in claim 1 wherein:

said polymer containing a fluorocarbon, comprises primarily a fluorocarbon polymer.

6. The valve described in claim 1 wherein:

said polymer containing a fluorocarbon, includes a first polymer that is not a fluorocarbon, and a fluorocarbon polymer filler mixed in said first polymer.

7. A fluid switching valve which includes stator and rotor elements with adjacent faces that press facewise against one another at an interface as said rotor element turns about an axis, with said stator element having a plurality of passage with proximal ends lying at said interface on a circle concentric with said axis and said rotor element having at least one groove with at least one groove end lying at said interface on said circle, wherein:

a first of said faces comprises a polymer containing a fluorocarbon, and the second of said faces contains tungsten carbide particles in an amorphous carbon matrix.

* * * * *